(12) United States Patent
Oguma et al.

(10) Patent No.: US 6,472,888 B2
(45) Date of Patent: Oct. 29, 2002

(54) BIOELECTRICAL IMPEDANCE MEASURING APPARATUS CONSTRUCTED BY ONE-CHIP INTEGRATED CIRCUIT

(75) Inventors: Koji Oguma, Fujisawa (JP); Tsutomu Miyoshi, Asaka (JP)

(73) Assignee: Tanita Corporation, Tokyo (JP)

( * ) Notice: Subject to any disclaimer, the term of this patent is extended or adjusted under 35 U.S.C. 154(b) by 0 days.

(21) Appl. No.: 09/770,607

(22) Filed: Jan. 29, 2001

(65) Prior Publication Data

US 2001/0010467 A1 Aug. 2, 2001

(30) Foreign Application Priority Data

Jan. 31, 2000 (JP) .......................... 2000-022395

(51) Int. Cl.[7] ............................ G01R 27/08; A61B 5/05
(52) U.S. Cl. ........................ 324/691; 324/692; 600/547
(58) Field of Search ................................ 324/691, 326, 324/318, 692; 600/506, 547

(56) References Cited

U.S. PATENT DOCUMENTS 6,151,523 A * 11/2000 Ferrer et al. ................ 600/506
6,201,990 B1 * 3/2001 Wexler et al. ............... 324/326

FOREIGN PATENT DOCUMENTS

| EP | 0 543 204 | 5/1993 |
| EP | 0 570 101 | 11/1993 |
| EP | 0 865 763 | 9/1998 |
| WO | WO99/52425 | 10/1999 |
| WO | WO99/58054 | 11/1999 |

* cited by examiner

*Primary Examiner*—N. Le
*Assistant Examiner*—James Kerveros
(74) *Attorney, Agent, or Firm*—McDermott, Will & Emery (57) ABSTRACT

The bioelectrical impedance measuring apparatus according to the present invention employs a microcomputer having almost all the functions necessary for the measurement of bioelectrical impedance integrated into a circuit on a one-chip. Further, the bioelectrical impedance measuring apparatus of the present invention employs also the one-chip microcomputer to provide almost all the functions necessary for the measurement at a plurality of frequencies or for that using a plurality of electrodes. Yet further, the bioelectrical impedance measuring apparatus of the present invention employs also the one-chip microcomputer to provide almost all the functions necessary for the measurement of other parameters, adding to those for measuring the bioelectrical impedance, using the external sensor connected thereto.

9 Claims, 5 Drawing Sheets

BIOELECTRICAL IMPEDANCE MEASURING APPARATUS CONSTRUCTED BY ONE-CHIP INTEGRATED CIRCUIT

FIELD OF THE INVENTION

The present invention relates to a measuring apparatus based on the bioelectrical impedance method, and in particular, to an improved circuit configuration of the apparatus constructed using an integrated circuit so as to be capable of measuring bioelectrical impedance.

DESCRIPTION OF THE PRIOR ART

An apparatus has been conventionally suggested and provided, which estimates a factor concerning to a body constitution based on the bioelectrical impedance method. There has been used, for example, a body fat meter which measures a bioelectrical impedance value of a living body of test subject by applying a current through end portions of the body of the test subject and measuring a voltage value between the portions of current application, and estimates a body fat rate from the measured value as well as a set of body data of the test subject including height, weight and sex, taken into account. An internal circuit of this body fat meter has been made up with a plurality of components including a microcomputer served as a control and processing unit (CPU), an operational amplifier, or the like.

The microcomputer employed in the above body fat meter has no functions other than those for the general microcomputer such as control and processing function, input/output ports or the like, leaving the other components to be arranged out of the microcomputer, connected thereto and controlled through respective ports.

In the body fat meter of the prior art, an alternating current generator section for generating an alternating current to be applied into a living body and outputting it therefrom, a differential amplifier for amplifying an analog signal outputted from the living body, an A/D converter for converting the analog signal from the differential amplifier to a digital signal, and the likes are entirely composed of a plurality of components arranged out of the microcomputer. Owing to this, sufficient amount of man-hour has to be used for mounting those components onto the circuit board. Further, disadvantageously the substrate of the body fat meter has necessarily increased in size, thus causing a negative effect that prevents the downsizing of the body fat meter itself.

Still further, since the analog signal obtained from the living body is inputted to, outputted from and processed by the differential amplifier and the A/D converter, which are connected via wiring patterns on the substrate, the signal is likely to be subject to interference by noise entering through the wiring patterns, resulting in an error in measuring of the bioelectrical impedance which otherwise should have been measured accurately.

Yet further, the body fat meter is often used in the relatively humid atmosphere such as in a bathroom or in a rest room, and sometimes the circuit board absorbs humid resulting in change of the dielectric constant, which may also cause an error in measuring the bioelectrical impedance. Accordingly, a level of accuracy in measurement of the bioelectrical impedance has been retained by taking such counter measure as employing a substrate with better humid-resistive characteristics to solve the problem of humidity.

Further disadvantageously, especially in such a body fat meter that is required to increase the number of measuring electrodes to increase the number of sites to be measured, or that is required to vary an alternating current applied into a living body to measure the bioelectrical impedance at a plurality of frequencies, a circuit configuration necessarily becomes more complicate and larger in size, which makes it much more difficult to downsize the body fat meter.

The present invention is made in the light of these problems described above and the object thereof is to provide a bioelectrical impedance measuring apparatus of high precision with low price, which has fewer number of circuit parts to reduce the number of manufacturing processes and thereby to reduce the cost therefor, and to provide a body fat meter employing said apparatus.

SUMMERY OF THE INVENTION

According to an aspect of the present invention, a bioelectrical impedance measuring apparatus for measuring a bioelectrical impedance of a test subject based on the bioelectrical impedance method, comprises an input device, an alternating current signal generating device, a switch, an amplifier, an analogue-to-digital converter, a control and processing device, a storage unit, an output device, and an oscillator, in which:

said input device inputs a personal body data of the test subject;

said alternating current signal generating device generates an alternating current signal to be applied to a living body;

said switch switches a connection to an electrode for measuring a voltage of the living body and that to a reference impedance to each other;

said amplifier amplifies a measured alternating voltage signal;

said analog-to-digital converter converts an analog value representative of amplified alternating voltage signal to a digital value;

said control and processing device estimates a factor concerning to a body constitution of the test subject based on the inputted personal body data and a measured bioelectrical impedance value, and controls each device;

said storage unit stores the inputted personal body data, the estimated factor concerning to the body constitution of the test subject, or the like;

said output device outputs a signal for indicating a set of estimated data concerning to the body constitution; and said oscillator generates a clock signal to actuate the control and processing device;

wherein said apparatus has a microcomputer including said alternating current signal generating device, said switch, said amplifier, said analog-to-digital converter, said control and processing device, said storage unit, said output device, and said oscillator integrated into a circuit on a one-chip.

A microcomputer employed in the bioelectrical impedance measuring apparatus according to the present invention further includes a divider and a frequency switching device, in which:

said divider generates an alternating current signal of multi-frequency; and said frequency switching device selectively outputs the alternating current signal of multi-frequency generated by said divider;

wherein both of said devices are also integrated into said circuit on said one-chip.

A microcomputer employed in the bioelectrical impedance measuring apparatus according to the present invention further includes a switch and another switch, in which;

said switch is connected to a plurality of power supply electrodes for measuring a bioelectrical impedance disposed out of said microcomputer, and switches alternating current signals from said alternating current power supply to output the signal therefrom; and said another switch is connected to a plurality of voltage detection electrodes disposed out of said microcomputer, and switches alternating voltages to be measured;

wherein both of said switches are also integrated into said circuit on said one-chip.

A microcomputer employed in the bioelectrical impedance measuring apparatus according to the present invention further includes a constant voltage generating device, a low voltage detecting device, a constant voltage supply device, a sensor input switching device, an amplifier; a converter, in which:

said constant voltage generating device is connected to a power supply disposed out of said microcomputer and generates a constant voltage;

said low voltage detecting device determines whether or not the level of voltage of said power supply disposed out of said microcomputer is on or over a specific level;

said constant voltage supply device supplies the constant voltage to a sensor disposed out of the microcomputer;

said sensor input switching device switches signals from the sensors disposed out of the microcomputer;

said amplifier amplifies an output signal from said sensor input switching device; and said converter converts an analog value representative of said amplified output signal to a digital value;

wherein all of said devices are also integrated into said circuit on said one-chip.

Further, said alternating current signal generating device comprises a storage unit, an output device, and a converter, in which:

said storage unit stores a sine wave voltage value;

said output device outputs a voltage signal based on said sine wave voltage value stored in said storage unit for each input of clock signal; and said converter converts a voltage signal to a current signal.

Further, said analog-to-digital converter comprises a calculator which calculates a digital value for every clock signal during a sampling period and measures an alternating voltage waveform to calculate an alternating voltage effective value.

Further, said alternating current signal generating device comprises a low pass filter and a voltage-to-current converter, in which:

said low pass filter removes high frequency components from an alternating square wave voltage outputted from said divider to convert it into a sine wave voltage; and said voltage-to-current converter converts said sine wave voltage to said alternating current signal to be applied to the living body.

Further, said analogue-to-digital converter comprises a rectifier, a filter circuit and a calculator, in which:

said rectifier rectifies the alternating voltage signal amplified by said amplifier;

said filter circuit makes said rectified alternating voltage signal be an effective value; and said calculator calculates a digital value from said signal made into effective value for each clock during sampling period.

There will be described in detail preferred embodiments of the present invention with reference to the accompanying drawings.

DESCRIPTION OF THE PREFERRED EMBODIMENTS

A bioelectrical impedance measuring apparatus according to the present invention employs a microcomputer having almost all the functions necessary for the measurement of bioelectrical impedance integrated into a circuit on a one-chip hereafter referred to as a one-chip microcomputer).

Further, the bioelectrical impedance measuring apparatus according to the present invention employs the one-chip microcomputer to provide almost all the functions necessary for the measurement at a plurality of frequencies or for that using a plurality of electrodes.

Further, the bioelectrical impedance measuring apparatus according to the present invention employs the one-chip microcomputer to provide almost all the functions necessary for the measurement of other parameters, adding to those for measuring the bioelectrical impedance, using the external sensor connected thereto.

A first embodiment of the present invention will be described with reference to the attached drawings.

Figure 1:
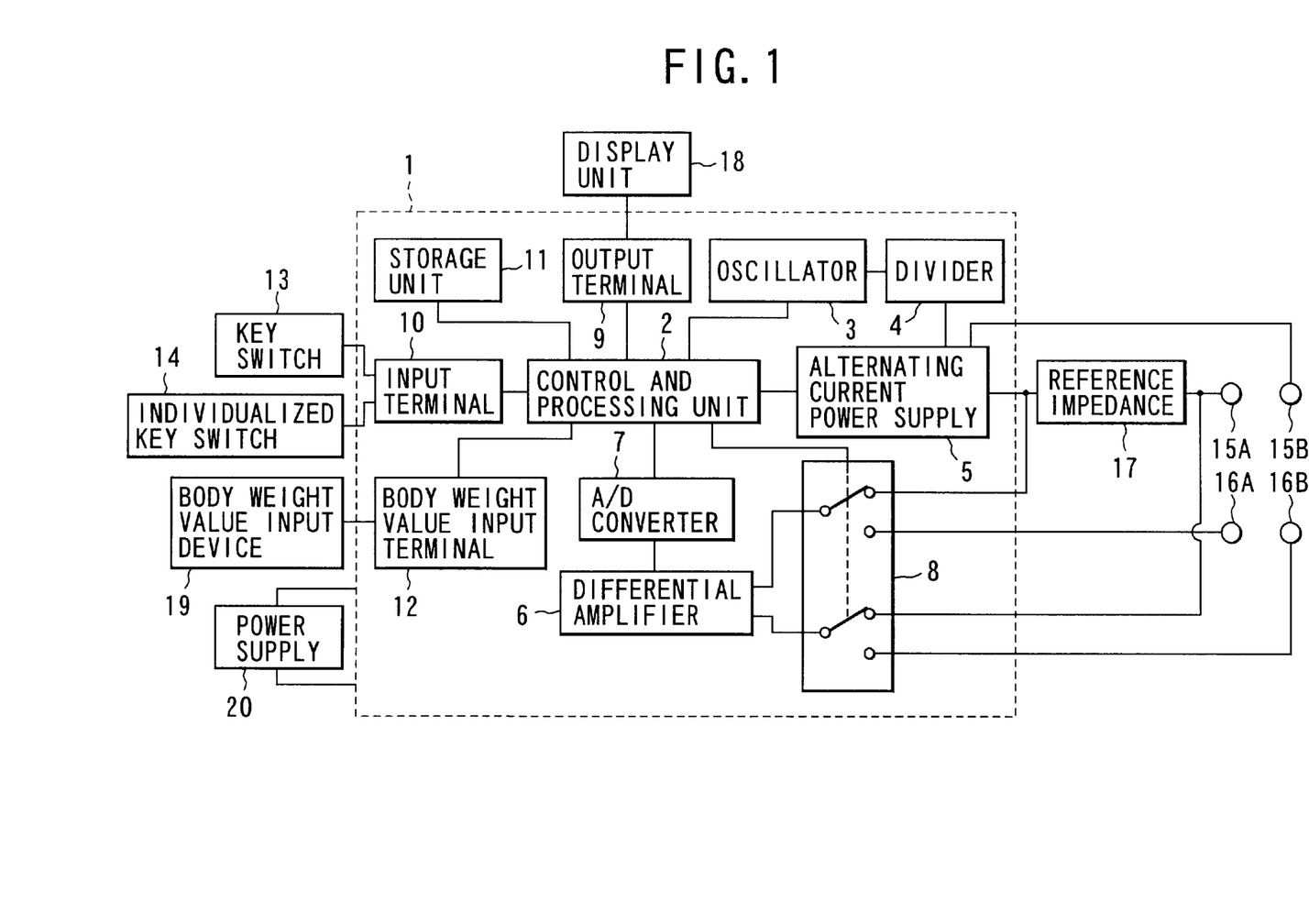
FIG. 1 is a block diagram illustrating an internal configuration of a body fat rate measuring apparatus of an embodiment according to the present invention.

FIG. 1 is a block diagram illustrating an electrical connection of an internal circuit of a body fat rate measuring apparatus of a first embodiment according to the present invention, which measures a body fat rate of a test subject based on a bioelectrical impedance thereof. Inside an one-chip microcomputer 1 of integrated circuit are included; a control and processing unit 2 served as a control means as well as a processing means for executing controlling and processing operations for respective elements; an oscillator 3 served as an oscillator means for generating a clock signal to be used for driving the control and processing unit 2; a divider 4 served as a divider means for dividing a frequency of the clock signal outputted from the oscillator 3; an alternating current power supply 5 served as an alternating current signal generator means for generating an alternating current from the divided frequency signal and outputting the alternating current to be applied to a living body; a differential amplifier 6 served as an amplifier means for amplifying a voltage signal generated in an impedance in the living body by the alternating current from said alternating current power supply 5 or a voltage signal generated in a reference impedance 17; an A/D converter 7 served as an analog to digital converter means for converting an analog value representative of the signal from said differential amplifier 6 to a digital value; a switching device 8 served as a switching means for switching a circuit under a control of the control and processing unit 2 so that either of the signal generated in the bioelectrical impedance or the signal generated in the reference impedance 17 may be inputted to the differential amplifier 6; an output terminal 9 provided as an output means for outputting a result to outside based on a bioelectrical impedance value calculated in the control and processing unit 2; an input terminal 10 comprising a plurality of ports provided for connecting with a switch group arranged out of the one-chip microcomputer 1, said switch group being served as an input means used for setting to start the measurement or setting the personal body data; a storage unit 11 served as a storage means for storing an operation program, the inputted personal body data, and the calculated bioelectrical impedance value; and a body weight value input terminal 12 which is used to input a body weight value of the test subject.

Outside of the one-chip microcomputer 1 are arranged; a switch group including, a key switch 13 which is used to set a personal body data such as a height, a sex, and an age of a test subject, and an individualized key switch 14 which is used to call out the set personal body data of each test subject from the storage unit 11 upon starting a measurement of a bioelectrical impedance; a pair of current supply electrodes 15A and 15B connected to the alternating current power supply 5 and to be brought into contact with the skin of the test subject to apply a current into the living body; a pair of voltage measuring electrodes 16A and 16B connected to the switching device 8 for measuring an voltage between respective sites to which the current has been applied; a reference impedance 17 which is used to measure the bioelectrical impedance value more accurately; a display unit 18 for indicating a result of measurement or contents of setting based on the signal from the output terminal 9; a body weight input device 19 connected to the body weight value input terminal 12 for inputting the body weight value of the test subject; and a power supply 20 connected to the one-chip microcomputer 1 for supplying a current to drive the whole circuit.

An operation of the internal circuit will now be described according to a measurement procedure of the present body fat rate measuring apparatus.

A person of test subject is requested to set a personal body data in advance by using the key switch 13. Upon starting a measurement, the test subject selects a personal number which has been assigned to his (her) personal data by the individualized key switch 14, and puts himself (herself) so that his (her) toes of soles of respective feet may come in contact with each of the current supply electrodes 15A, 15B and his (her) heels may come in contact with each of the voltage measuring electrodes 16A, 16B respectively.

In response to an input from the individualized key switch 14, the control and processing unit 2 commands the divider 4 to generate a desired frequency signal using a clock signal from the oscillator 3 and also commands the alternating current power supply 5 to generate a alternating constant current to be applied to a living body. The generated alternating constant current is applied into the body of the test subject via the current supply electrodes 1SA and 15B.

The control and processing unit 2 having the reference impedance 17 measured in advance, herein actuates the switching device 8 to complete the circuit for the voltage measuring electrodes 16A and 16B to measure the bioelectrical impedance value in the living body. Since the bioelectrical impedance measuring method using this reference impedance has been disclosed in the Japanese Patent Laid-open Publication No. H6-277191 filed by the present applicant, a detailed description will be omitted herein. The measured bioelectrical impedance signal is amplified by the differential amplifier 6. An analog value representative of this amplified bioelectrical impedance signal is converted to a digital value by the A/D converter 7 to be inputted to the control and processing unit 2.

The control and processing unit 2, based on the personal number selected by the individualized key switch 14, reads out the personal body data stored in the storage unit 11, calculates a body fat rate of the test subject from the digital signal of bioelectrical impedance outputted from the A/D converter 7, the body data and the body weight value of the test subject inputted through the body weight value input device 19 connected to the body weight value input terminal 12, and sends an output signal to the output terminal 9 for indication of the result. This body weight value input device 19 may be a body weight sensor which actually measures the body weight of a test subject, or may be of such device configured such that a numerical value is inputted through a key operation. The output signal from the output terminal 9 is transmitted to the display unit 18 to indicate the result.

Although some exemplary configurations of the alternating current power supply 5 will now be described, it would be appreciated that these have been commonly employed and accordingly the description should be given in brief.

Figure 2A:
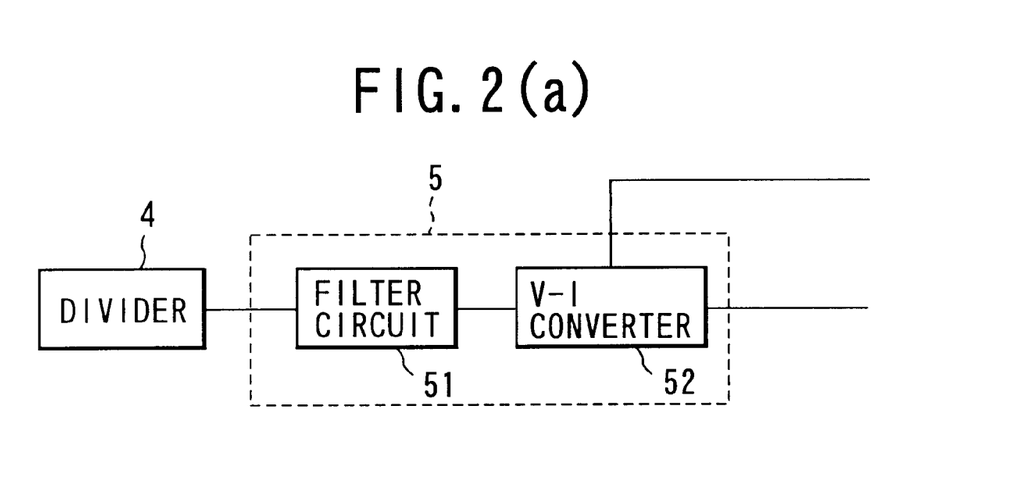
FIGS. 2(a) and 2(b) are a block diagram illustrating a configuration of an alternating current power supply of an embodiment according to the present invention.

FIG. 2(*a*) is a block diagram of an internal configuration of the alternating current power supply 5 and the peripheral devices, and what will be explained herein generates a sine wave alternating current of 50 kHz.

A crystal oscillator is used for the oscillator 3 to output a square wave oscillation signal at some MHz. In this embodiment, a clock square wave oscillation signal of 3,2 MHz is formed into a square wave alternating voltage of 50 kHz by using a divider 4 with a dividing ratio of 1/64. A filter circuit 51 of the alternating current power supply 5 is a low pass filter which eliminates high frequency components to convert the square wave voltage into a sine wave voltage. Since a condenser employed in this circuit preferably has a large capacity, it may be arranged out of the one-chip microcomputer 1.

The sine wave voltage of alternating current of 50 kHz is converted in a V-I converter 52 from the alternating voltage to an alternating current to generate a constant current sine wave.

Figure 2B:
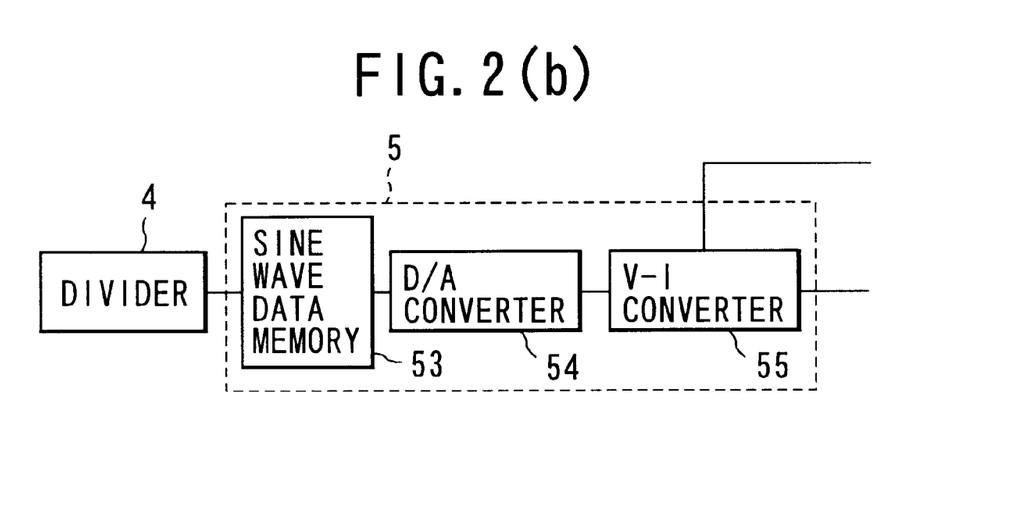

Alternatively, the alternating current power supply 5 may be configured without filter circuit as shown in FIG. 2(*b*). In this case, a waveform of alternating sine wave of 50 kHz is divided by n along the time axis, and a voltage value data for each divided section is stored in a sine wave data memory 53. Based on this voltage data stored in this sine wave data memory, a D/A converter 54 outputs a signal every time when a clock signal from the divider 4 is inputted. Thereby an output waveform could be a proximate sine wave, thus to generate a sine wave alternating voltage of 50 kHz.

The sine wave voltage of alternating current of 50 kHz is converted in a V-I converter 55 from the alternating voltage to an alternating current to generate an alternating current to be applied to a living body. By taking advantage of this configuration to generate a constant current sine wave, a condenser with large capacity required by the filter circuit would not be necessary any more, thus allowing to facilitate the integration of one-chip microcomputer.

Although the divider 4 is arranged between the oscillator 3 and the alternating current power supply 5, it should be readily understood that the divider 4 might be eliminated in such configuration that enables the sine wave data memory to store a large volume of voltage value data so that the clock signal from the oscillator 3 may be directly used for processing.

Then some exemplary configurations of the A/D converter 7 will be described, but the description therefor will be made in brief since these have been also commonly employed.

Figure 3A:
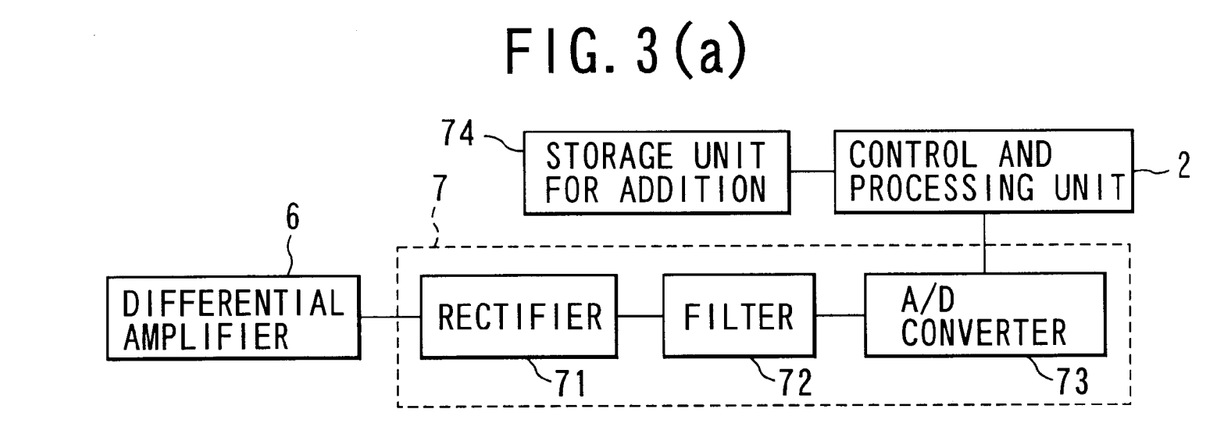
FIGS. 3(a) and 3(b) are a block diagram illustrating a configuration of an A/D converter of an embodiment according to the present invention.

FIG. 3(a) is a block diagram illustrating internal components of an A/D converter 7 and peripheral devices connected thereto. An alternating voltage signal from the differential amplifier 7 is half-wave- or full-wave-rectified in a rectifier 71. A rectified alternating voltage signal is made to be an effective value in a filter circuit 72; the value in turn is A/D converted for every clock during a sampling period in an A/D converting section 73 controlled by the control and processing unit 2; the measured values are accumulatively stored in a storage for addition 74 in the storage unit 11; and then the control and processing unit 2 sums up the stored values to determine the mean value thereof.

Figure 3B:
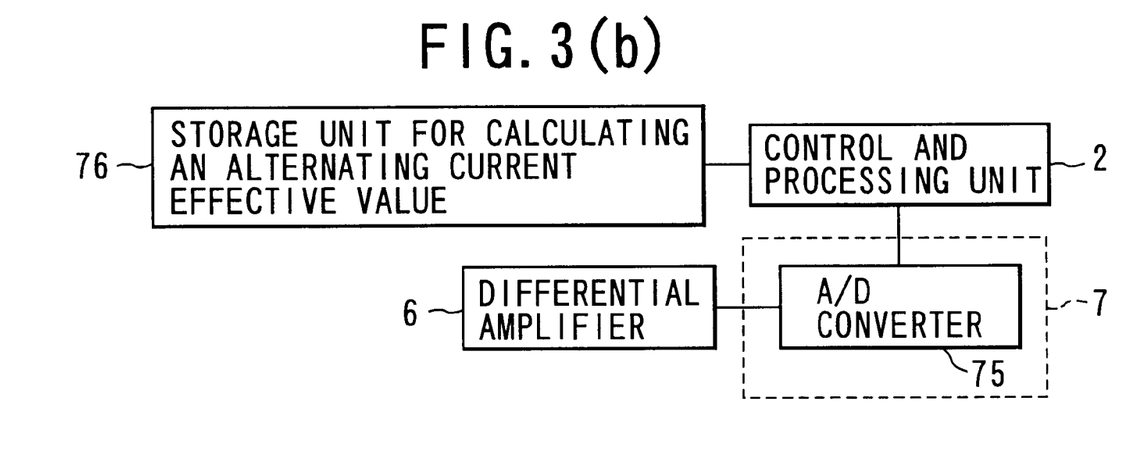

In an A/D converter 7 shown in FIG. 3(b), an alternating voltage signal from the differential amplifier 6 is A/D converted for every clock during a sampling period to determine a converted value, which in turn is used to calculate an alternating current effective value. That is, an A/D converting section 75 controlled by the control and processing unit 2 processes the input alternative voltage signal for each clock to determine an alternating voltage value at that time and the determined values are accumulatively stored in a storage 76 for calculating an alternating current effective value. Based on the stored voltage values, an alternating voltage waveform is estimated to determine a maximum voltage value and to calculate an alternating voltage effective value. The A/D converting section 75 employed herein is faster than the A/D converting section 73 employed in FIG. 3(a).

Figure 4:
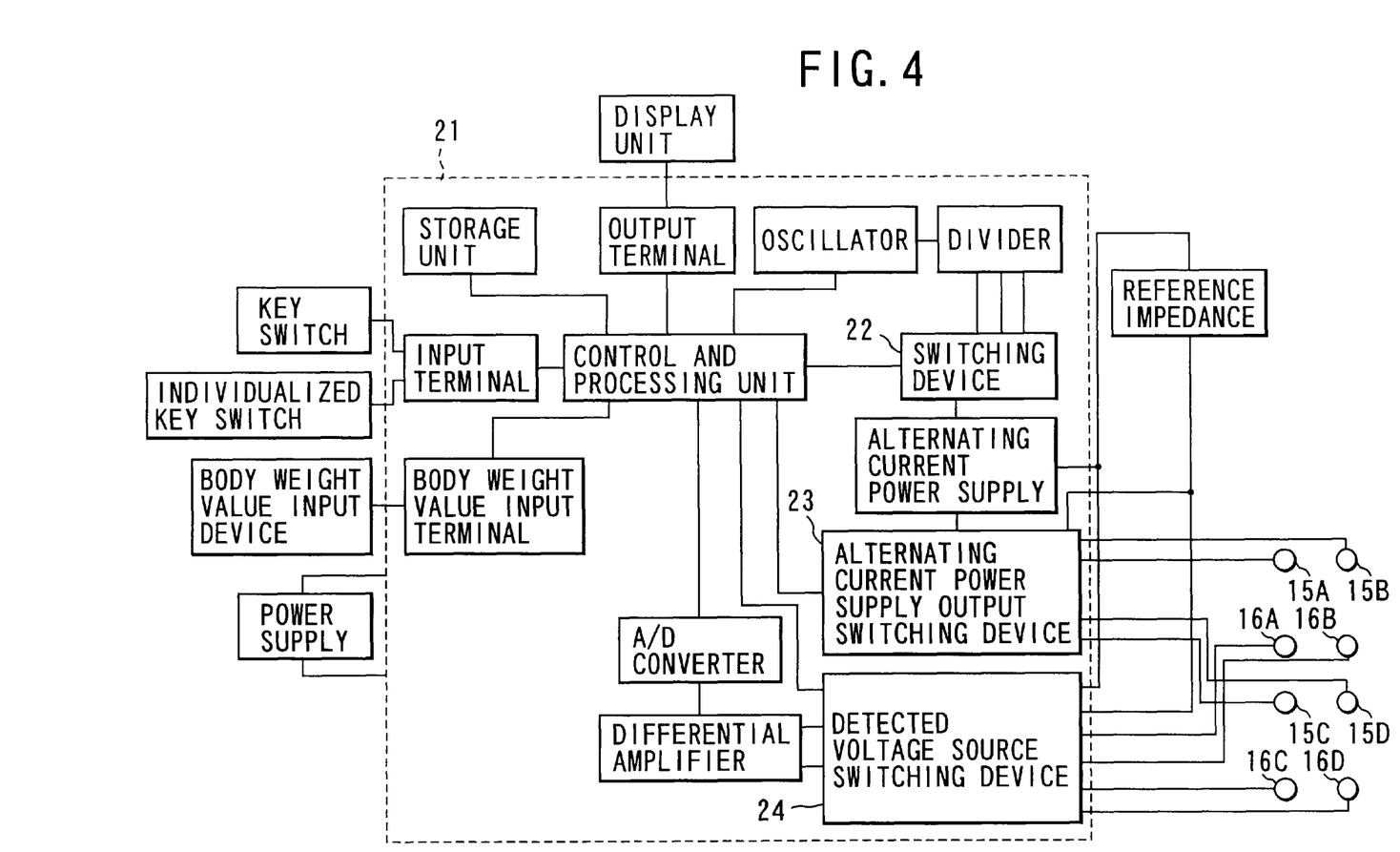
FIG. 4 is a block diagram illustrating an internal configuration of a body fat rate measuring apparatus of an alternative embodiment according to the present invention.

As a second embodiment of the present invention, a bioelectrical impedance measuring apparatus shown in FIG. 4 will be described. This apparatus further comprises within a one-chip microcomputer 21, in addition to a plurality of blocks shown in the first embodiment: a divider 4 modified as a divider means within the one-chip microcomputer 21 for outputting a plurality of frequencies based on a plurality of dividing ratios so that the frequency of alternating current outputted from an alternating current power supply 5 could be adaptively varied; a switching device 22 served as a switching means arranged between said divider 4 and the alternating current power supply 5; an alternating current power supply output switching device 23 served as a switch means for switching output alternating current signals and connected with a plurality of current supplying electrodes 15A to 15D; and a detected voltage source switching device 24 served as a switch means for switching an alternating voltage and a reference impedance to each other and connected with a plurality of voltage detecting electrodes 16A to 16D; so hat the bioelectrical impedance may be measured at a plurality of frequencies and in a plurality of sites using a plurality of electrodes.

A pulse signal outputted from the oscillator 3 is sent to the divider 4 to generate a pulse signal, which is a plurality of frequencies. The generated multifrequency pulse signals are sent to the switching device 22 controlled by the control and processing unit 2 so that the frequency of the output signal could be varied. The output signal from the switching device 22 is converted by the alternating current power supply 5 shown in above mentioned FIG. 2(a) or FIG. 2(b) from a square alternating wave signal to a constant current sine wave to be applied to a living body, and is inputted to the alternating current power supply output switching device 23.

The alternating power supply output switching device 23 connects with four current supply electrodes 15A to 15D. These four current supply electrodes 15A to 15D are respectively brought into contact with, for example, both hands and both feet of four limbs of human body. Similarly, the detected voltage source switching deice 24 connects with four voltage detecting electrodes 16A to 16D, which are also brought into contact with both hands and both feet respectively. Thus, the configuration employing a plurality of electrodes allows the bioelectrical impedance to be measured, for example, between hands, between feet, and between a hand and a foot, and thereby to obtain readily a body fat rate of respective region.

Further, the switching device 22 can vary the frequency of output signal to allow the bioelectrical impedance to be measured at a plurality of frequencies. Thereby, it is allowed to estimate more factors concerning to a body constitution, such as an inter-cellular water(ICW), an extra-cellular water (ECW), a ratio of the inter-cellular water to the extra-cellular water, a total body water(TBW), a body fat mass, and a fat free mass(FFM) of respective region.

Figure 5:
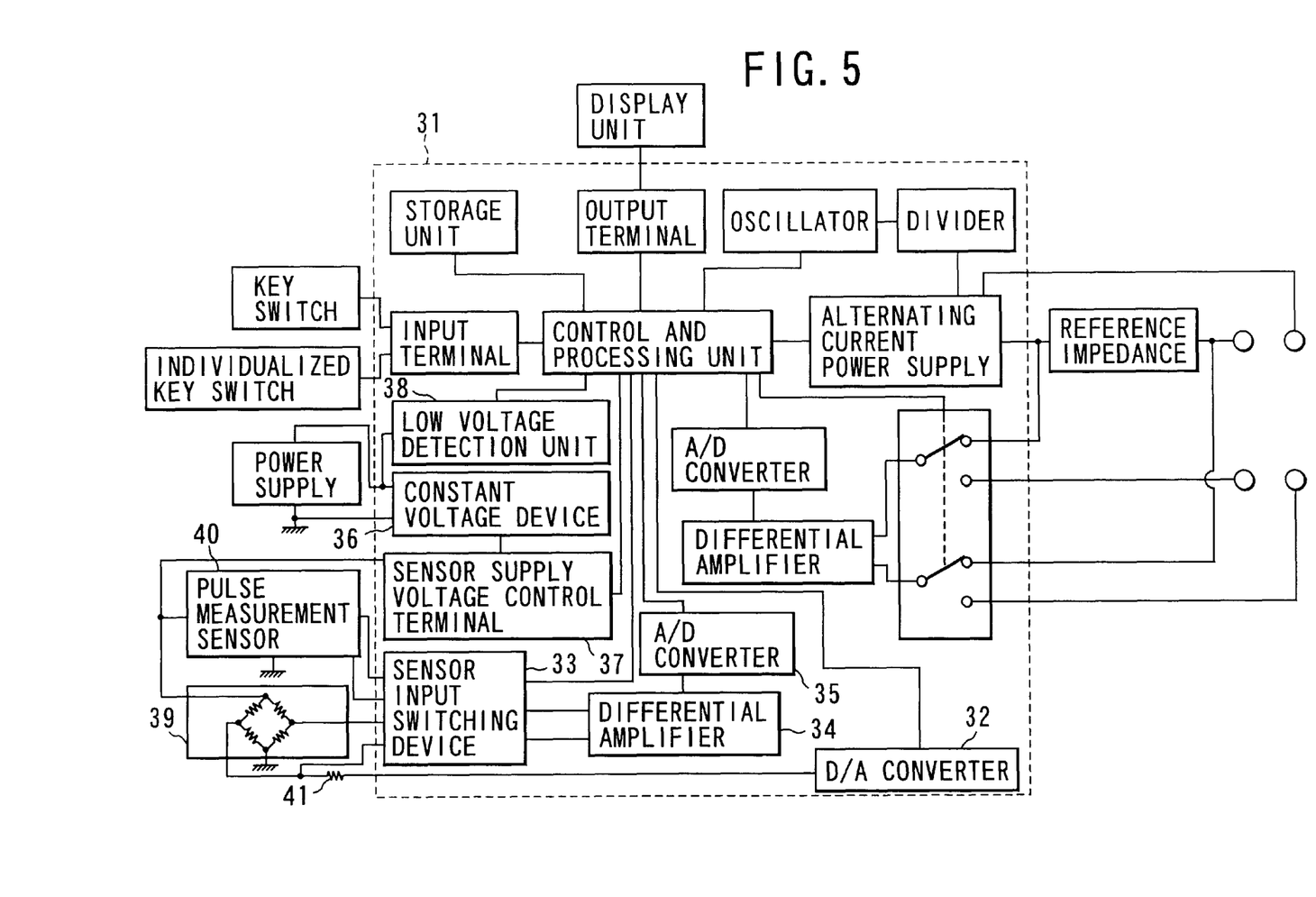
FIG. 5 is a block diagram illustrating an internal configuration of a body fat rate measuring apparatus of another alternative embodiment according to the present invention.

As a third embodiment of the present invention, a bioelectrical impedance measuring apparatus shown in FIG. 5 will now be described. FIG. 5 is a block diagram of the bioelectrical impedance measuring apparatus further comprising outside a one-chip microcomputer 31, in addition to a plurality of blocks described in the first embodiment: a sensor 39 for measuring a body weight; and another sensor 40 for measuring pulse, both of said sensors being provided as external sensors; so that the body weight and the pulse may be simultaneously measured together with the bioelectrical impedance.

This apparatus further comprises within the one-chip microcomputer 31, in addition to a plurality of blocks shown in the first embodiment: a D/A converter 32 for supplying an analog voltage via a resistor 41 to an external sensor; a sensor input switching device 33 controlled by the control and processing unit 2 for switching inputs from external sensors; a differential amplifier 34 served as an amplifier means for amplifying a signal outputted from an external sensor; an A/D converter 35 served as a converter means for converting an analog value representative of a sensor output signal outputted from the differential amplifier 34 to a digital value; a constant voltage output device 36 connected to the power supply 20 and served as a constant voltage generation means for outputting a constant voltage; a sensor supply voltage controller 37 served as a constant voltage supply means for supplying each sensor with an output voltage from the constant voltage output device 36; and a low voltage detection device 38 served as a low voltage detection means for determining if the output voltage from the constant voltage output device 36 is not under the predetermined level of voltage; wherein said apparatus yet further comprises, as external sensors, a sensor 39 for measuring a body weight and another sensor 40 for measuring pulse.

In the bioelectrical impedance measuring apparatus of this configuration, the body weight measurement sensor 39 is supplied with the constant voltage generated by the constant voltage output device 36 from the sensor supply voltage controlling terminal 37 at the same time when the test subject measures the bioelectrical impedance.

A bridge circuit in the body weight measurement sensor 39 outputs a voltage signal corresponding to the weight of the test subject. This output voltage is inputted to the differential amplifier 34 via the sensor input switching device 33 to be amplified, and the amplified voltage signal is converted by the A/D converter 35 from the analog signal to the digital signal to determine the body weight. At that time, an operational amplifier within the differential amplifier 34 has an offset voltage, and thereby, even if the output from the bridge circuit is zero, the output of the differential amplifier 34 does not necessarily indicate zero due to this offset voltage. To cope with this problem, the D/A converter 32 is provided so that an analog signal for automatically regulating the offset voltage in the operational amplifier within the differential amplifier 34 may be outputted via a resistor 41 to the bridge circuit of the body weight measurement sensor.

When the measurement of the body weight has been completed, the pulse measurement sensor 40 is in turn activated, and accordingly the sensor input switching device 33 is also connected to the pulse measurement sensor 40. Herein, as similar to the measurement of the body weight, an output signal concerning to a pulse of a living body is inputted via the differential amplifier 34 and the A/D converter 35 to the control and processing unit 2 to calculate the number of pulses of the test subject.

The configuration described above allows a measurement concerning to other factors of a living body as well as a measurement of bioelectrical impedance to be executed on a one-chip microcomputer according to the present invention.

Although the embodiments of the present invention have been described as above with reference to an apparatus for principally estimating and indicating a body fat rate based on a measured bioelectrical impedance value, it should be appreciated that since the bioelectrical impedance measuring apparatus according to the present invention has employed a one-chip microcomputer in the form of integrated circuit having a plurality of functions necessary for measuring the bioelectrical impedance, the application thereof is not limited to those embodiments but the apparatus may be used to estimate other factors of body constitution, including the total body water and a muscle mass, based on the measured bioelectrical impedance value.

Further, although the present embodiments have been described with reference to the configuration employing an alternating current as the output signal from the alternating current power supply 5, the configuration of the alternating current power supply 5 is not limited to this but an alternating voltage may be used to measure the bioelectrical impedance. It should be noted that the configuration employing the alternating current voltage for measurement has been disclosed in the Japanese Patent Laid-open Publication No. H11-113873 filed by the present applicant.

Since a bioelectrical impedance measuring apparatus of the present invention comprises a one-chip microcomputer having internally a plurality of functions necessary for the measurement of bioelectrical impedance integrated thereinto, therefore the number of parts could get fewer to reduce the number of faults in parts and the management cost thereof, and further the number of pins to be soldered to a substrate could get fewer to reduce the number of faults in soldering and the time needed for mounting of the circuit parts to the substrate.

Besides, since the area of substrate could be reduced, the water content possibly absorbed in the substrate depending on humidity would inevitably decrease, and still further, since the number of wiring patterns for connecting parts on the circuit board could be reduced, the bioelectrical impedance would be measured accurately with little interference otherwise possibly caused by the humidity or the noise.

Yet further, since a bioelectrical impedance measuring apparatus itself could be downsized, the apparatus would become applicable to the measurement in the specific sites or to the other purposes, to which the measurement has conventionally been difficult to be applied.

Still further, even in the case where the number of measuring electrodes is required to be increased to increase the number of sites to be measured, or an alternating current to be applied to the body is required to be varied to measure the bioelectrical impedance at a plurality of frequencies, or in the case where an external sensor is required to be connected to measure other parameters concerning to a body constitution of a test subject simultaneously together with the bioelectrical impedance, the bioelectrical impedance measuring apparatus employing a one-chip microcomputer according to the present invention comprising all of the necessary circuit parts integrated therein would eliminate the increase in scale of circuit, which otherwise possibly may cause more complexity and increase in size of the circuit configuration.

Yet further, a filter circuit which needs a capacitor with large capacity could be eliminated to facilitate the integration of one-chip microcomputer when such a configuration is employed as an alternating current power supply for generating alternating current to be applied to the living body, which comprises a storage means for storing a sine wave voltage value, and an output means for outputting a voltage signal based on the sine wave voltage value stored in the storage means in response to each input of clock signal, wherein an alternating current is generated by a converter means for converting the voltage signal to a current signal.

Still further, the integration of one-chip microcomputer is also facilitated in the case where such a configuration is employed as an A/D converter, in which a digital value is calculated for each clock signal during sampling period to estimate an alternating voltage waveform and thus to calculate an alternating voltage effective value, which consequently allows the analogue value to be converted to the digital value with simplified circuit configuration.

What is claimed is:

1. A bioelectrical impedance measuring apparatus for measuring a bioelectrical impedance of a test subject based on the bioelectrical impedance method, comprising:

an input device which inputs a personal body data of the test subject;

at least a pair of current supply electrodes for applying a current into a living body, at least a pair of voltage measuring electrodes for measuring a voltage of the living body, a display unit for indicating a result of measurement, and a one-chip microcomputer including an alternating current signal generating device, an amplifier, an analog-to-digital converter, a control and processing device, a storage unit, an output terminal and an oscillator, wherein:

said alternating current signal generating device generates an alternating current signal to be applied to a living body through said current supply electrodes;

said amplifier amplifies a measured alternating voltage signal;

said analog-to-digital converter converts an analog value representative of said amplified alternating voltage signal to a digital value;

said control and processing device estimates a factor relating to a body constitution of the test subject based on the inputted personal body data and a measured bioelectrical impedance value, and controls each device;

said storage unit stores the inputted personal body data, the estimated factor concerning the body constitution of the test subject, or the like;

said output terminal outputs a signal for indicating a set of estimated data concerning the body constitution; and said oscillator generates a clock signal to actuate the control and processing device.

2. A bioelectrical impedance measuring apparatus in accordance with claim 1 further comprising a body weight input device for inputting the body weight value of the test subject.

3. A bioelectrical impedance measuring apparatus in accordance with claim 1 or 2, in which said one-chip microcomputer further includes a divider and a frequency switching device, in which:

said divider generates an alternating current signal of multi-frequency; and said frequency switching device selectively outputs the alternating current signal of multi-frequency generated by said divider.

4. A bioelectrical impedance measuring apparatus in accordance with any one of claims 1 or 2, in which said one-chip microcomputer further includes a switch and another switch, in which;

said switch is connected to a plurality of power supply electrodes for measuring a bioelectrical impedance disposed out of said one-chip microcomputer, and switches alternating current signals from said alternating current power supply to output the signal therefrom; and said another switch is connected to a plurality of voltage detection electrodes disposed out of said one-chip microcomputer, and switches alternating voltages to be measured.

5. A bioelectrical impedance measuring apparatus in accordance with any one of claims 1 or 2, in which said one-chip microcomputer further includes a constant voltage generating device, a low voltage detecting device, a constant voltage supply device, a sensor input switching device, an amplifier, a converter, in which:

said constant voltage generating device is connected to a power supply disposed out of said microcomputer and generates a constant voltage;

said low voltage detecting device determines whether or not the level of voltage of said power supply disposed out of said one-chip microcomputer is on or over a specific level; said constant voltage supply device supplies the constant voltage to a sensor disposed out of the one-chip microcomputer;

said sensor input switching device switches signals from the sensors disposed out of the microcomputer;

said amplifier amplifies an output signal from said sensor input switching device; and said converter converts an analog value representative of said amplified output signal to a digital value.

6. A bioelectrical impedance measuring apparatus in accordance with any one of claims 1 or 2, in which said alternating current signal generating device comprises a storage unit, an output device, and a converter, in which:

said storage unit stores a sine wave voltage value;

said output device outputs a voltage signal based on said sine wave voltage value stored in said storage unit for each input of clock signal; and said converter converts said voltage signal to a current signal.

7. A bioelectric impedance measuring apparatus in accordance with any one of claims 1 or 2, in which said analog-to-digital converter comprises a calculator which calculates a digital value for every clock signal during a sampling period and measures an alternating voltage waveform to calculate an alternating voltage effective value.

8. A bioelectrical impedance measuring apparatus in accordance with any one of claims 1 or 2, in which said alternating current signal generating device comprises a low pass filter and a voltage-to-current converter, in which:

said low pass filter removes high frequency components from an alternating square wave voltage outputted from said divider to convert it into a sine wave voltage; and said voltage-to-current converter converts said sine wave voltage to said alternating current signal to be applied to the living body.

9. A bioelectrical impedance measuring apparatus in accordance with any one of claims 1 or 2, in which said analogue-to-digital converter comprises a rectifier, a filter circuit and a calculator, in which:

said rectifier rectifies the alternating voltage signal amplified by said amplifier said filter circuit makes said rectified alternating voltage signal be an effective value; and said calculator calculates a digital value from said signal made into effective value for each clock during sampling period.

* * * * *